(12) United States Patent
Eder et al.

(10) Patent No.: US 6,585,753 B2
(45) Date of Patent: Jul. 1, 2003

(54) EXPANDABLE COIL STENT

(75) Inventors: Joseph C. Eder, Los Altos Hills, CA (US); Lex P. Jansen, Pleasanton, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 20 days.

(21) Appl. No.: 09/681,394

(22) Filed: Mar. 28, 2001

(65) Prior Publication Data

US 2002/0151966 A1 Oct. 17, 2002

(51) Int. Cl.$^7$ .................................................. A61F 2/06
(52) U.S. Cl. ..................... 623/1.15; 623/1.18; 623/1.22
(58) Field of Search ............................... 623/1.15–1.22

(56) References Cited

U.S. PATENT DOCUMENTS

| | | | | |
|---|---|---|---|---|
| 4,553,545 | A | 11/1985 | Maass et al. ................ 128/341 |
| 4,856,516 | A | 8/1989 | Hillstead .................... 128/343 |
| 4,886,062 | A | 12/1989 | Wiktor ....................... 128/343 |
| 4,954,126 | A | 9/1990 | Wallsten ....................... 600/36 |
| 5,116,365 | A | * 5/1992 | Hillstead ................... 623/1.15 |
| 5,183,085 | A | * 2/1993 | Timmermans ............. 623/1.15 |
| 5,342,300 | A | 8/1994 | Stefanadis et al. ............ 604/95 |
| 5,554,181 | A | 9/1996 | Das ................................ 623/1 |
| 5,591,198 | A | * 1/1997 | Boyle et al. ................ 606/198 |
| 5,591,230 | A | * 1/1997 | Horn et al. ................. 623/1.15 |
| 5,782,907 | A | 7/1998 | Frantzen et al. ................ 623/1 |
| 5,795,318 | A | 8/1998 | Wang et al. ..................... 604/8 |
| 5,807,404 | A | 9/1998 | Richter .......................... 623/1 |
| 5,868,780 | A | 2/1999 | Lashinski et al. ............ 606/198 |
| 5,902,266 | A | 5/1999 | Leone et al. ................... 604/53 |
| 5,902,317 | A | 5/1999 | Kleshinski et al. ......... 606/198 |
| 5,938,697 | A | 8/1999 | Killion et al. .................. 623/1 |
| 5,964,771 | A | 10/1999 | Beyar et al. ................. 606/108 |
| 6,053,940 | A | * 4/2000 | Wijay ......................... 623/1.16 |
| 6,080,190 | A | * 6/2000 | Schwartz .................... 623/1.15 |
| 6,168,621 | B1 | 1/2001 | Vrba ............................ 623/1.2 |
| 6,171,338 | B1 | * 1/2001 | Talja et al. ................. 623/11.11 |
| 6,214,042 | B1 | * 4/2001 | Jacobsen et al. ............. 623/1.2 |
| 6,165,178 | A1 | 12/2001 | Bashiri et al. ............... 606/108 |
| 6,355,058 | B1 | * 3/2002 | Pacetti et al. .............. 623/1.15 |
| 6,361,558 | B1 | * 3/2002 | Hieshima et al. .......... 623/1.16 |
| 6,428,570 | B1 | * 8/2002 | Globerman ................ 623/1.15 |

FOREIGN PATENT DOCUMENTS

| | | |
|---|---|---|
| DE | 196 34 241 A1 | 2/1998 |
| DE | 297 21 310 | 3/1998 |
| WO | 95/31945 | 11/1995 |
| WO | 97/37615 | 10/1997 |
| WO | 01/01888 | 1/2001 |
| WO | 01/08600 | 2/2001 |
| WO | 01/45593 | 6/2001 |

OTHER PUBLICATIONS

Kutryk, Michael J.B., "Coronary Stenting: Current Perspectives," *A Companion to the Handbook of Coronary Stents*, pp. 53–59 (1999).

Rodriguez, Alfredo, "The Gianturco–Roubin II (GRII) Stent," *Handbook of Coronary Stents*, pp. 9–15 (Second Edition 1998).

Beyar, Rafael, "The Coronary Cardiocoil," *Handbook of Coronary Stents*, pp. 243–253 (Second Edition 1998).

\* cited by examiner

*Primary Examiner*—David H. Willse
*Assistant Examiner*—Suzette J. Jackson
(74) *Attorney, Agent, or Firm*—Vidas, Arrett & Steinkraus

(57) ABSTRACT

An implantable coil stent comprises at least a first curved segment and a curved segment which arc about the longitudinal axis of the stent. An expandable link extends between the second end of the first curved segment and the first end the second curved segment.

30 Claims, 4 Drawing Sheets

EXPANDABLE COIL STENT

BACKGROUND OF INVENTION

The use of stents to maintain the patency of bodily lumens is well known. are typically delivered via a catheter in an unexpanded configuration to a desired bodily location. Once at the desired bodily location, the stent is expanded and implanted in the bodily lumen. The stent may self-expand or may be mechanically expanded. Where a self-expanding stent is used, the stent is typically retained on the catheter via a retention device such as a sheath. The stent may be deployed by retracting the sheath from over the stent. Where a mechanically expandable stent used, a radially outward force is typically applied to the stent to expand it. The may be applied via an expandable member such as a balloon or via any other mechanical device.

Stents are used in an array of bodily vessels including the coronary arteries, the peripheral arteries, arteries of the neck, cerebral arteries, veins, biliary ducts, urethras, ureters, fallopian tubes, bronchial tubes, the trachea, the esophagus and the prostate.

Currently available stents include tubular stents such as the NIR™ stent as well as coil stents. Tubular stents are typically formed from tubes or from sheets of material from which material has been removed to form openings.

Coil stents typically are formed of a wire or strand which has been wound into coil shape. Coil stents can exhibit a high degree of flexibility, including bendability and longitudinal flexibility which facilitates delivery of the stent through tortuous bodily vessels. Accurate sizing of coil stents, however, can be quite challenging.

There remains a need for coil stents which are flexible and which can be easily and accurately sized to the vessels in which they are implanted.

All U.S. patents and applications and all other published documents mentioned anywhere in this application are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as only for the purposes of complying with 37 C.F.R. 1.72. The abstract is not to be used for interpreting the scope of the claims.

SUMMARY OF INVENTION

In one embodiment, the invention is directed to an implantable coil stent comprising a first curved segment and a second curved segment and an link extending between the first and second curved segments. The first and second curved segments arc about the longitudinal axis of the stent. Desirably, the expandable link has at least one bend therein.

Where the stent comprises a plurality of expandable links including a first expandable link and a second expandable link, desirably the second expandable is spaced along the stent from the first expandable link by at least 90 degrees and more desirably, by at least 180 degrees.

Desirably, the expandable segment is made of a first material and the curved segment of a second material. The first material may be stainless steel and the second material may be nitinol. Other combinations are also within the scope of invention. Optionally, the curved segments are in the form of one or more wires having an outer layer of material and a radiopaque core.

The invention is also directed to a coil stent comprising a first segment which curves about the longitudinal axis of the stent, a third segment which curves about the longitudinal axis of the stent and a second segment disposed between the first and third segments where the first and third segments are formed of a first and the second segment is formed of a second material different from the first material. The first, second and third segments are joined end-to-end. Desirably, second segment has at least one bend therein. The second segment may have a plurality of bends therein.

The first material desirably is a shape memory material and the second desirably is stainless steel. The first material may be adhesively joined to the material or joined via any other suitable technique.

The invention is further directed to a medical coil implant for implantation in a bodily vessel. The implant comprises a strand having a plurality of winding which wind about the longitudinal axis of the implant and a plurality of linking segments, the linking segments extending between winding segments which are adjacent one another along the coil. Each linking segment has at least one bend. Desirably, the linking segments are made of a first material and the winding segments are made of a second material different from the first material. Winding segments which are adjacent to linking segments may be adhesively bonded soldered thereto or joined by any other suitable techniques.

It is also within the scope of the invention for the linking segments and the winding segments to be made from the same material, the linking segments been subjected to a different treatment than the winding segments. The linking segments and the winding segments may optionally be made of a shape memory material, for example nitinol. The shape memory material in the linking segments may be subjected to a different heat treatment or annealing than the shape material in the winding segments. The medical coil implant may be provided in the form of a stent, vena cava filter or vaso-occlusive device.

The invention is also directed to any of the inventive medical devices disclosed herein in combination with a medical balloon, where the medical device is disposed about the medical balloon.

The invention is further directed to methods of deploying any of the inventive medical devices disclosed herein at a desired bodily location. In accordance with embodiment of the invention, a medical device delivery catheter comprising any of the inventive medical devices disclosed herein is provided. The catheter is in a bodily vessel to a desired location in the body and the inventive medical device caused to expand to a first size. The expandable links are then expanded to expand the medical device to a second size. The expansion of the expandable links may be accomplished by inflating a medical balloon or expanding any other mechanical expansion device disposed within the inventive medical device or via other suitable method.

Additional details and/or embodiments of the invention are discussed below.

BRIEF DESCRIPTION OF DRAWINGS

FIG. 1b shows an enlarged view of portion 1b of the coil stent of FIG. 1a.

DETAILED DESCRIPTION

Figure 1A:
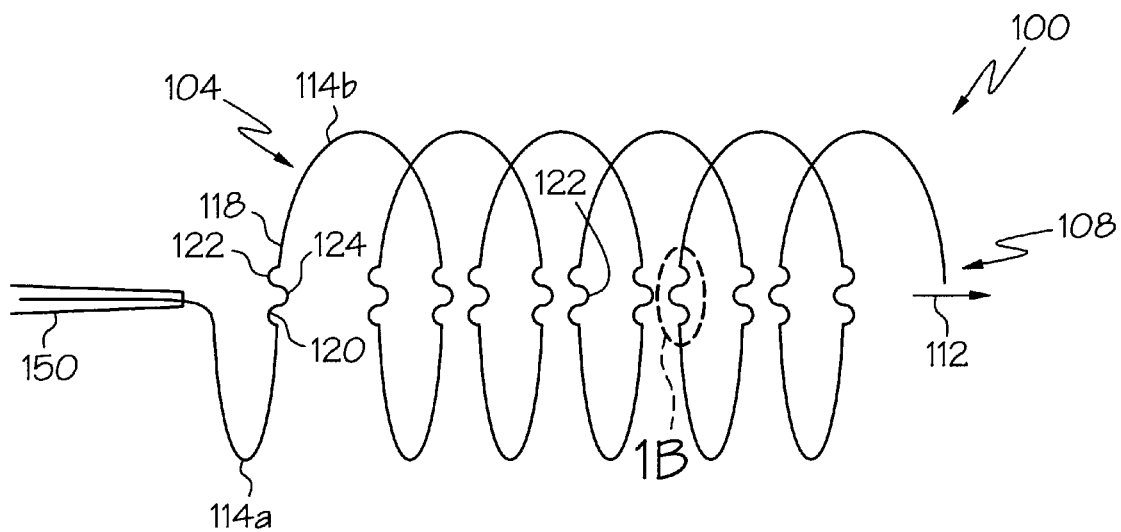
FIG. 1a is a side view of a coil stent in accordance with the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

With reference to FIG. 1a, the invention is directed, in one embodiment, to an implantable coil stent such as that shown generally at 100 in FIG. 1a. Coil stent 100 is shown in FIG. 1a as it is being deployed from catheter 150. Coil stent 100 has a proximal end 104, a distal end 108 and a longitudinal axis 112 therethrough. Coil stent 100 comprises first curved segment 114a and second curved segment 114b. First curved segment 114a and second curved segment 114b arc about axis 112 of stent 100. First curved segment 114a and second curved segment have a first end 118 and a second end 120. Stent 100 further comprises link 122 extending between second end 120 of first curved segment 114a and first end 118 of second curved segment 114b. As shown in FIG. 1, expandable link 122 has a plurality of bends 124 therein. The invention contemplates embodiments in which the expandable segment has a single bend and embodiments in which the expandable sections has a serpentine or other bent appearance.

Figure 1B:
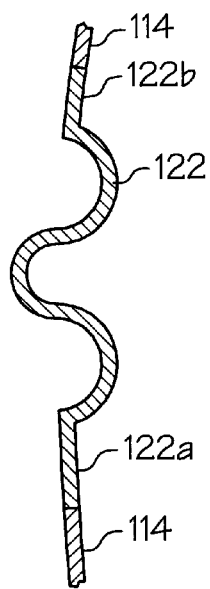

Desirably, as shown in the expanded view of FIG. 1b, the curvature of expandable links 122 at each end 122a and 122b is substantially similar to the curvature of the ends of the curved segments 114 to avoid an excess concentration of stress at junctions between the expandable links and the curved segments.

The coil stent of FIG. 1a comprises a plurality of expandable links 122. nearest neighboring expandable links along the stent are spaced by at least 90 degrees about the longitudinal axis of the stent and more desirably, as shown in 1a, by at least 180 degrees about the longitudinal axis of the stent.

Coil stents comprising a single expandable link are also within the scope of the invention and any of the embodiment disclosed herein may be provided with a expandable link.

Figure 2:
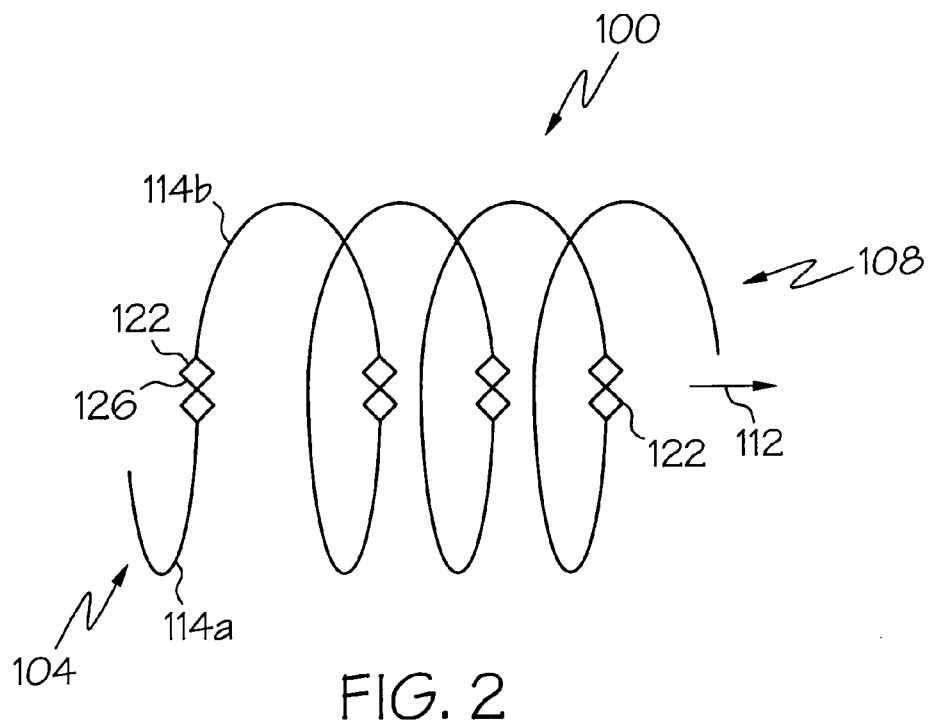
FIG. 2 is a side view of a coil stent in accordance with the invention.

The invention also contemplates other forms for the expandable link. For example, as shown in FIG. 2, expandable link 122 comprises at least one cell 126 and desirably, a plurality of expandable cells 126. Cells 126 are diamond shaped. Cells of any other suitable, expandable shape may be used as well. For example, the cells may rectangular or may be defined by a curved shape.

Desirably, as shown in FIG. 2, at least one expandable link is provided per one complete turn of the stent about the longitudinal axis. More desirably, between and four expandable links are provided per turn of the stent. Stated otherwise, nearest neighboring expandable links along the stent desirably are spaced by between about 90 degrees and 360 degrees apart about the longitudinal axis of stent. In other embodiments of the invention, the stents may have more than four expandable links per turn or less than one expandable link per turn of the stent. an example of the latter, one expandable link may be provided for every two turns the stent about the longitudinal axis of the stent.

It is also within the scope of the invention to provide a coil stent having at least one expandable link similar to that disclosed in conjunction with FIG. 1a and at one expandable link similar to that disclosed in conjunction with FIG. 2.

In one embodiment of the invention, the expandable links may be made of stainless steel and the curved segments made of a shape memory material. shape memory materials include shape memory metals such as nitinol. More generally, the expandable links may be made of a first material and the curved segments made of a second material different from the first material. The expandable links and the curved segments may be joined end-to-end adhesively, soldering, welding, laser welding, the use of plasma techniques, the use of electron beams or via any other suitable technique. Suitable adhesives include and epoxies. Desirably, the curvature of the ends of the expandable links will be substantially similar to the curvature of the ends of the curved segments to avoid excess concentration of stress at junctions between the expandable links and the curved segments.

The invention is also directed to a coil stent, such as that shown at 100 in FIG. 1a, comprising three segments. The three segments include: first curved segment 114a which curves about longitudinal axis 112 of the stent, second curved segment 114b which curves about the longitudinal axis of the stent and expandable link 122 disposed between first curved segment 114a and second curved segment 114b where first curved segments and second curved segments are formed of a first material and expandable links are formed of a second material different than the first material or differently treated than the first material. The three segments are joined end-to-end. Desirably, as shown in FIG. 1a, expandable link 122 has at least one bend therein. Optionally, expandable link 122 may have a plurality of bends therein.

Desirably, the first material is a shape memory material and the second is stainless steel. The shape memory material may be metal or polymeric. An example of a suitable shape memory material is nitinol. Other suitable metals for use in the inventive stents disclosed herein include L605, MP35N and other metals having a composition of Co 45%–55% by weight, Cr 15%–25% by weight, W 12%–18.0% by weight, Ni 8%–12% by weight, Fe 1%–3% by weight and Mn 1%–2% by weight. L605 has a high modulus of elasticity and is sufficiently radiopaque to it to be seen under fluoroscopy. L605 is also MRI (magnetic resonance imaging) compatible. It is noted that L605 may be used in the manufacture of stents of any other known stent designs as well including coil cells and stents comprising a plurality of interconnected bands. L605 may desirably be employed as the second material. The second material may also be a polymeric material. Another suitable second material is nitinol whose superelastic properties have been destroyed.

The first material and second materials may be adhesively joined, joined via soldering, welding, laser welding or any of the other techniques disclosed herein or via any other suitable technique.

The invention is also directed to a medical coil implant, such as that shown at 100 in FIG. 1a, for implantation in a bodily vessel. The implant comprises a strand having a plurality of winding segments 114*a,b* which wind about the longitudinal axis of the implant and a plurality of linking segments 122. Linking segments 122 extend between winding segments 114*a,b* which are adjacent one another with linking segment 122 having at least one bend.

In one embodiment, the linking segments are made of a first material and the winding segments are made of a second material different from the first material. For example, the winding segments may be made of a shape memory material, for example, nitinol and the second material may be made of stainless steel. Adjacent winding and linking segments may be fused one to the other, for example by soldering, or adhesively bonded one to the other or joined together via any of the other modalities discussed in this disclosure.

In another embodiment of the invention, the linking segments (or expandable segments) and the winding segments are made from the same material where the linking segments (or expandable segments) have been subjected to a different treatment than the winding segments. For example, the linking segments (or expandable segments) may have been differently annealed than the winding segments, differently heat treated or subject to a different chemical treatment. The implant may be made from a shape memory material where the shape memory of the linking segments (or expandable segments) has been destroyed by being to a different treatment than the winding segments. Heat treatment typical for superelastic material such as nitinol occurs in the range of 500° C. By heating nitinol based linking segments to temperatures substantially in excess of 500° C. and just below the melting point of about 1300° C., the superelastic properties of the linking material will be destroyed. Such a treatment may be accomplished by first heat treating the entirety of the shape memory material to set the shape of the coil and then by selectively heat treating the linking members to destroy the superelastic properties of the linking members.

Desirably, the curvature of the ends of the linking segments will be similar to the curvature of the ends of the winding segments to avoid an excess concentration of stress at junctions between the linking segments and the winding segments.

Where the stent comprises individual segments which are joined together, and the various segments are subject to different treatments, heat, chemical or otherwise, the shape of the individual segments may be set prior to, during or subsequent to joining the segments together.

Similarly, where the stent is formed from a continuous strand or strip of material, segments of which are subjected to different treatments, the shape of the stent may be established prior to, during or subsequent to the treatment of the material.

Figure 3:
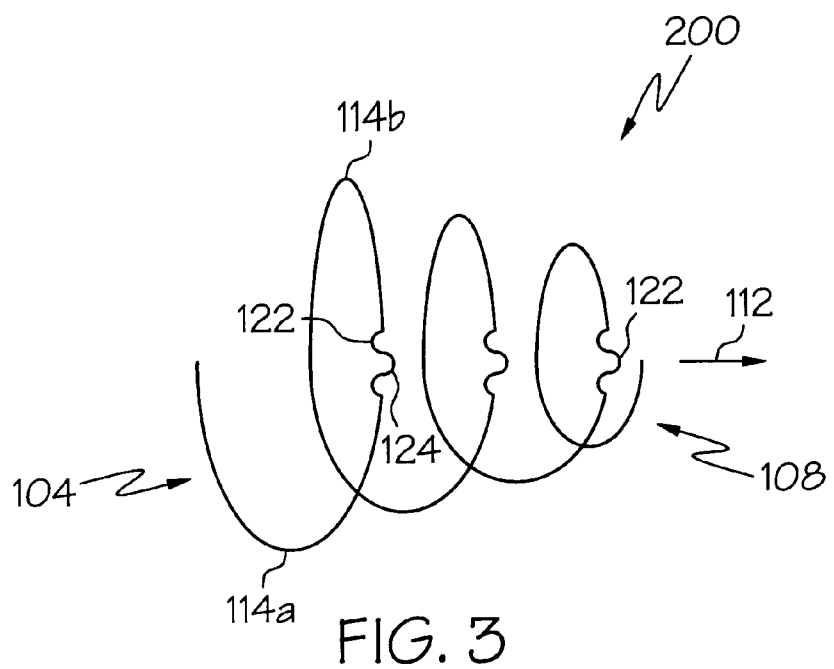
FIG. 3 is a side view of a vena cava filter in accordance with the invention.

The inventive implant may be made in the form of a stent as shown in FIGS. 1 and 2, in the form of a vena cava filter, shown generally at 200 in FIG. 3 or in the form of a vaso-occlusive device. To that end, any of the coil based vaso-occlusive devices disclosed in U.S. Pat. No. 6,165,178 may be provided with expandable segments as disclosed herein.

Vena cava filters and vaso-occlusive devices may also be provided with an expandable link in the form of one or more cells such as those discussed in conjunction with FIG. 2 above.

Desirably, the expandable links or linking segments of any of the medical devices disclosed herein will be constructed to allow for up to a 100% additional radial expansion or more of the medical device following initial expansion of the medical device to the maximum diameter attainable by expansion of the curved segments. The extent of the additional expansion provided by the expandable or linking segments will depend on the choice of materials and the design of the expandable links or linking segments. For example, where the expandable link or linking segment comprises a plurality of bends, the extent of the additional expansion provided by the expandable link or linking segment will depend on the total length of the expandable link or linking segment when it is unbent and on the extent to which the expandable link or linking segment unbends during expansion.

Any of the inventive stents disclosed herein may be constructed and arranged that at least a portion of the stent tapers when the stent is in the expanded state. The stent may taper from one end to the other end or a portion of the stent may have a taper and the remainder of the stent be of constant diameter in the state. The stent may include one or more portions of increasing diameter which are followed by one or more portions of decreasing diameter in the expanded state.

The inventive stents disclosed herein may be constructed of any size and be of any diameter suitable for use in a bodily vessel. Desirably, the inventive stents will range in length from about 6 mm to about 100 mm. Also desirably, the inventive stents will, in the expanded state, range in diameter from about 1.5 mm to about mm. The expandable links will desirably allow up to a doubling or more of the diameter of the stent beyond the maximum diameter attainable by expansion of curved segments of the stent.

As discussed above, in any of the inventive medical devices (e.g. stents, grafts, vena cava filters, vaso-occlusive devices and other coil based medical devices) disclosed herein, at junctions where segments of different material are joined together, or junctions where adjacent segments are differently treated, the of the adjacent ends of the adjacent segments will desirably be substantially to one another to avoid an excess concentration of stress at the junctions between the expandable links and the curved segments.

The inventive medical devices disclosed herein in various of the embodiments may be entirely mechanically expandable, for example via the use of a medical balloon, or may be partially self-expanding. The self-expanding mechanism may achieved through the use of a suitably treated shape memory material for the or winding segments or through the use of a resilient or spring-like material for curved or winding segments. In other embodiments of the invention, the inventive medical devices may be entirely mechanically expandable.

The invention is also directed to grafts where the inventive stents disclosed herein serve as the framework. Any suitable graft materials may be used including collagen, polyethylene terephthalate (PET), polyethylene, polypropylene, polytetrafluoroethylene (PTFE), expanded polytetrafluoroethylene and any other suitable polymeric material. Metal foils may also be disposed about the stent framework.

It is noted, for the purposes of this disclosure, that the term "bend" does not refer to a specific method of construction. For example, the expandable links and more specifically the bent segments may be formed by laser cutting or chemically etching a curved pattern in a material. The expandable links may also be formed by physically bending a wire or other piece of material.

The inventive medical devices may include suitable radiopaque coatings. For example, the inventive medical devices may be coated with gold or other noble metals or sputtered with tantalum or other metals. The inventive medical devices may also be made directly from a radiopaque material to obviate the need for a radiopaque coating or may be made of a material having a radiopaque inner core. For example, the inventive medical devices may be made of nitinol disposed about platinum core. Such a construction is disclosed in U.S. Pat. No. 6,165,178. Any of the other coil materials and constructions disclosed in U.S. Pat. No. 6,165,178 for coils may also be employed in the inventive medical devices disclosed herein. Other radiopaque which may be used include platinum, platinum-tungsten, palladium, platinum-iridium, rhodium, tantalum, or alloys or composites of these metals.

The inventive medical devices may also be provided with various bio-coatings to enhance various properties of the inventive medical devices. For example, the inventive medical devices may be provided with lubricious coatings or other polymeric coatings. The inventive medical devices may also be provided with drug-containing coatings which release drugs over time. An example of a suitable polymeric coating is PTFE.

The inventive medical devices may also be provided with a sugar or more generally a carbohydrate and/or a gelatin to maintain the inventive medical devices on a balloon during delivery of the medical device to a desired bodily location. suitable compounds for treating the inventive medical devices include polymers and polymers which are dissolvable in bodily fluids. Portions of the and/or exterior of the inventive medical devices may be coated or impregnated the compound. Mechanical retention devices may also be used to maintain the inventive medical devices on the balloon during delivery.

The inventive stents may find use in the coronary arteries, the peripheral arteries, arteries of the neck and the cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate. The inventive stents may be used interarterially in the brain, deployed across the neck of an aneurysm as well as in occlusions in vessels.

The invention is also directed to a method of implanting a stent comprising the steps of providing a stent delivery catheter, the catheter comprising a coil stent in accordance with the present invention, advancing the catheter in a bodily vessel to desired location in the body and deploying the stent at the desired bodily location. The catheter may then be withdrawn.

Where the stent has self-expanding characteristics, the stent may be held in place on the catheter via a restraint such as a sheath. The sheath may then be retracted to deploy the stent. An additional force may be applied to the stent via an expandable device such as a balloon in order to complete the deployment of the stent. The balloon may be used to apply a force to the stent and thereby expand expandable link(s).

Figure 4:
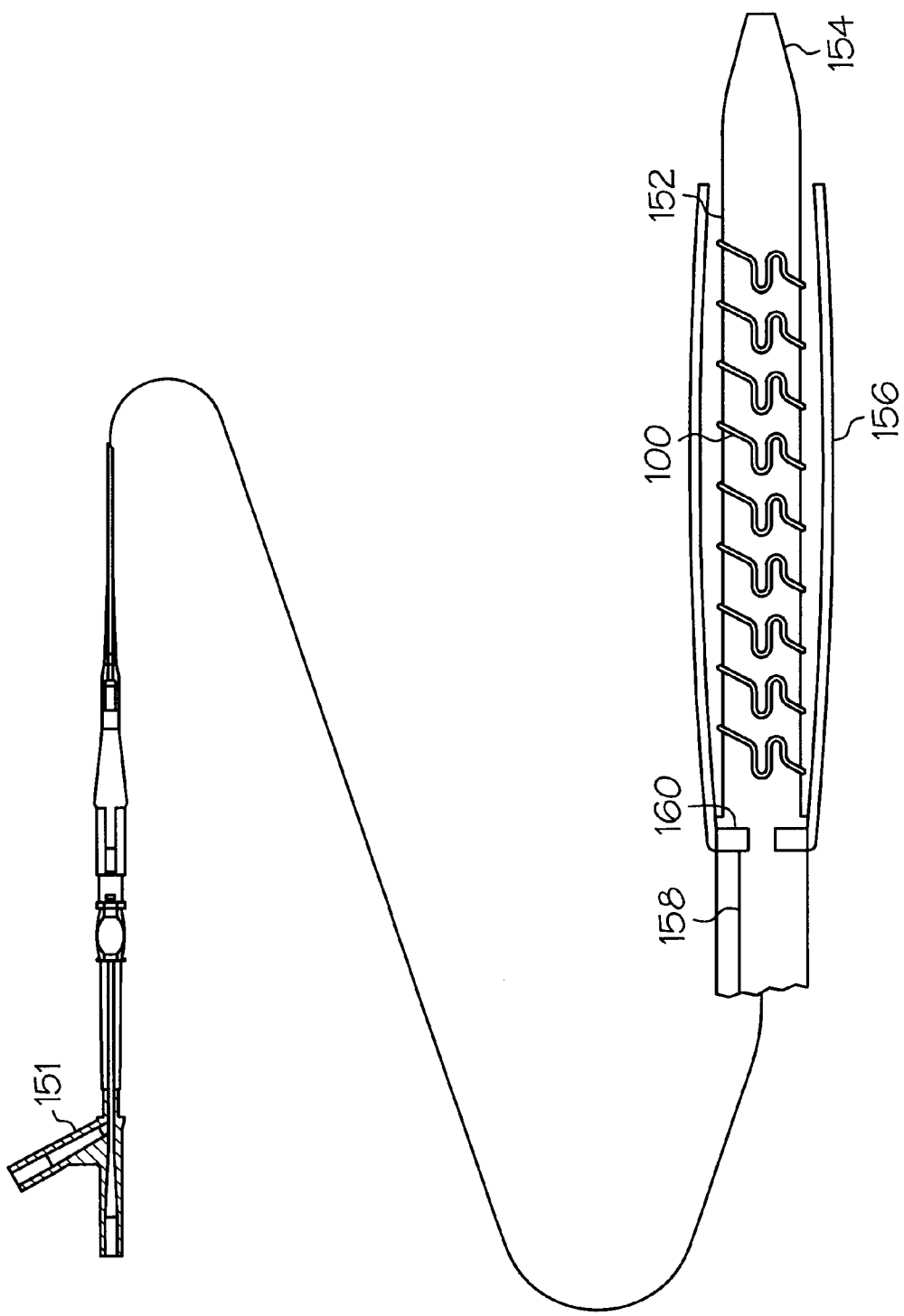
FIG. 4 is a side view of a catheter with an inventive stent disposed thereabout with parts cut away.

In accordance with the inventive method, a stent delivery catheter such as that shown generally at 150 in FIG. 4. Catheter 150 includes a manifold 151 at the proximal end and an inner tube 152 which terminates in a tip 154 at the distal end. Stent 100 is disposed about the distal end of inner tube 152. Stent 100 may be any of the inventive stents disclosed herein. Retractable sheath 156 covers stent 100. Pull collar 160 is attached to retractable sheath 156. Pull wire 158 extends from collar 160 to the proximal end of the catheter.

Figure 5:
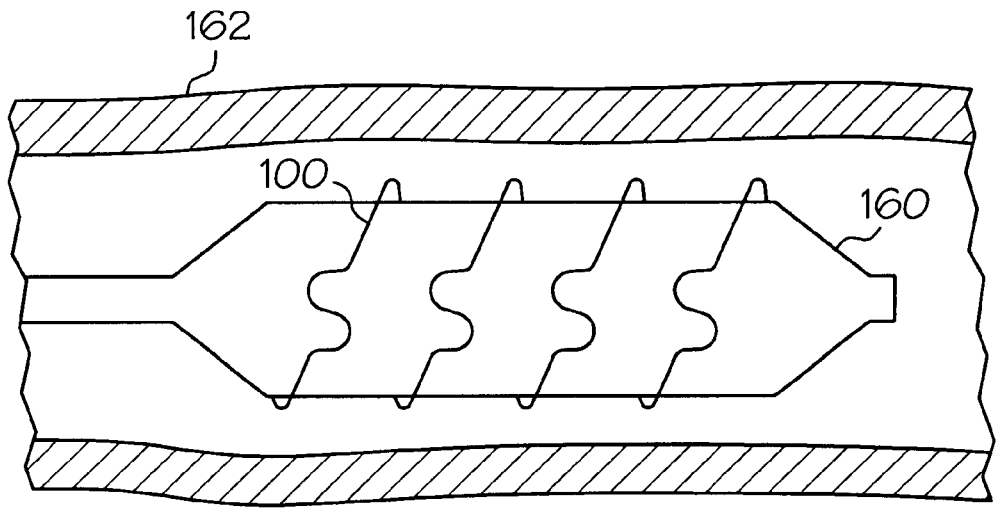
FIG. 5 is a side view of an inventive stent disposed about a balloon catheter in a bodily vessel.
Figure 6:
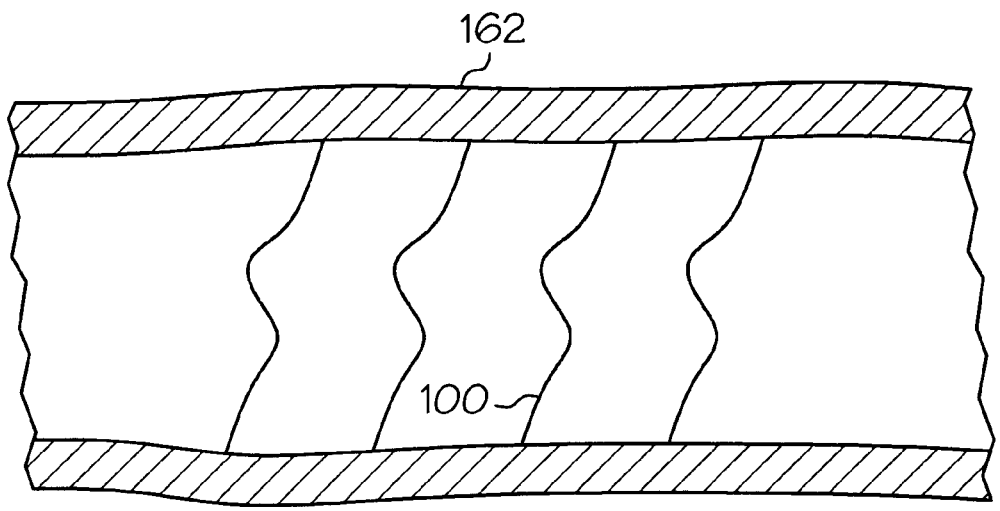
FIG. 6 is a side view of an inventive stent seated in a vessel.

The distal end of catheter 100 is inserted in a bodily vessel and advanced to a desired location in the body. Retractable sheath 156 is retracted by pulling proximally on pull wire 158. As retractable sheath 156 is retracted, stent 100 expands and is deployed. Catheter 150 may be withdrawn and, as shown in FIG. 5, balloon catheter 160 advanced and positioned with deployed stent 100. Stent 100 FIG. 5 is not fully expanded. Balloon catheter 160 is then inflated thereby the expandable links and seating the stent in the desired location in bodily vessel 162. The balloon catheter is then withdrawn. The seated stent is shown schematically in FIG. 6. Desirably, the expandable links will be constructed and arranged to allow for up to 100% additional radial expansion of the stent.

It is also within the scope of the invention to use a stent delivery catheter includes a balloon so that the stent may be seated without the need to withdraw stent delivery catheter and insert a balloon catheter. The catheter of FIG. 4 may be modified by including a balloon disposed between the stent and the inner tube and including an inflation lumen in fluid communication with the balloon.

The inventive stents may also be delivered through a microcatheter and post inflated with a medical balloon.

More generally, the invention is further directed to methods of deploying any the inventive medical device at a desired bodily location. In accordance with one embodiment of the invention, a medical device delivery catheter, comprising any of the inventive medical devices disclosed herein is provided. The catheter is in a bodily vessel to a desired location in the body and the inventive medical device caused to expand to a first size. The expandable links are then expanded to expand the inventive medical device to a second size. The expansion of the expandable links may be accomplished by inflating a medical balloon or expanding any other mechanical expansion device disposed within the inventive medical or via any other suitable method. In accordance with the invention, the inventive medical devices may also be delivered through a microcatheter and post inflated with a medical balloon.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple form from all prior claims which possess all antecedents referenced in such dependent claim if such multiple dependent format is an accepted format within jurisdiction (e.g. each claim depending directly from claim 1 should be alternatively taken as depending from all previous claims). In jurisdictions where multiple dependent claim formats are restricted, the following dependent claims should be also taken as alternatively written in each singly dependent claim format which creates a dependency from a prior antecedent-possessing claim other than the specific claim listed in such dependent claim below (e.g. claim 3 may be taken as alternatively dependent from claim 1; claim 4 may be taken as alternatively dependent on claim 1, or on claim 2; etc.).

The disclosure is intended to be illustrative and not exhaustive. This will suggest many variations and alternatives to one of ordinary skill in this art. All these alternatives and variations are intended to be included within the scope of attached claims. Those familiar with the art may recognize other equivalents to the specific embodiments described herein which equivalents are also intended to be encompassed by the claims attached hereto.

What is claimed is:

1. A coil stent comprising a first curved segment and a second curved segment, the first and second curved segments arcing about the longitudinal axis of the stent, each of the first and second curved segments having a first end and a second end, the stent further comprising an expandable link extending between the second end of the first curved segment and the first end of the second curved segment, wherein the curved segments are made of shape memory alloys or shape memory polymers and the expandable link is made of a different material than that of the curved segments.

2. The coil stent of claim 1 wherein the expandable link has at least one bend therein.

3. The coil stent of claim 2 comprising a plurality of expandable links, each link having at least one bend therein.

4. The coil stent of claim 3 wherein the plurality of expandable links includes first expandable link and a second expandable link, the second expandable link spaced along the stent from the first expandable link by at least 90 degrees.

5. The coil stent of claim 3 wherein the plurality of expandable links includes first expandable link and a second expandable link, the second expandable link spaced along the stent from the first expandable link by at least 180 degrees.

6. The coil stent of claim 1 wherein the expandable segment is made of stainless steel and the curved segments are made of nitinol.

7. A coil stent comprising a first curved segment and a second curved segment, the first and second curved segments arcing about the longitudinal axis of the stent, each of the first and second curved segments having a first end and a second end, the stent further comprising an expandable link extending between the second end of the first curved segment and the first end of the second curved segment, wherein the curved segments are in the form of a wire having an outer layer of material and a radiopaque core.

8. In combination, the coil stent of claim 1 and a medical balloon, the coil stent disposed about the medical balloon.

9. A coil stent having a longitudinal axis, the stent comprising a first segment which curves about the longitudinal axis of the stent, a third segment which curves about the longitudinal axis of the stent and a second segment disposed between the first and third segments, the first and third segments formed of a first material, the second segment formed of a second material different from the first material, the first, second and third segments joined end-to-end.

10. The coil stent of claim 9 wherein the second segment has at least one bend therein.

11. The coil stent of claim 10 wherein the first material is a shape memory material and the second material is stainless steel.

12. The coil stent of claim 11 wherein the first material is adhesively joined to the second material.

13. The coil stent of claim 9 where the second segment has a plurality of bends therein.

14. In combination, the coil stent of claim 9 and a medical balloon, the coil stent disposed about the medical balloon.

15. A medical coil implant for implantation in a bodily vessel, the implant having a longitudinal axis, the implant comprising a strand having a plurality of winding segments which wind about the longitudinal axis of the implant and a plurality of linking segments, the linking segments extending between winding segments which are adjacent one another, each linking segment having at least one bend wherein the linking segments are made of a first material and the winding segments are made of a second material different from the first material.

16. A medical coil implant for implantation in a bodily vessel, the implant having a longitudinal axis, the implant comprising a strand having a plurally of winding segments which wind about the longitudinal axis of the implant and a plurality of linking segments, the linking segments extending between winding segments which are adjacent one another, each linking segment having at least one bend wherein the linking segments and the winding segments are made from the same material, the linking segments having been subjected to a different treatment than the winding segments.

17. The medical coil implant of claim 16 wherein the linking segments and winding segments are made of a shape memory material.

18. The medical coil implant of claim 17 wherein the shape memory material the linking segments has been subject to a different heat treatment than shape memory material in the winding segments.

19. The medical coil implant of claim 17 wherein the shape memory material the linking segments has been subject to a different annealing treatment the shape memory material in the winding segments.

20. The medical coil implant of claim 17 wherein the shape memory material nitinol.

21. The medical coil implant of claim 15 in the form of a stent.

22. The medical coil implant of claim 15 in the form of a vena cava filter.

23. The medical coil implant of claim 15 wherein winding segments which are adjacent to linking segments are adhesively bonded thereto.

24. The medical coil implant of claim 15 wherein winding segments which are adjacent to linking segments are soldered thereto.

25. The medical coil implant of claim 15 wherein the linking segments are made of L605.

26. In combination, the coil stent of claim 15 and a medical balloon, the coil stent disposed about the medical balloon.

27. A method of deploying a stent at desired bodily location comprising the steps of: providing a stent delivery catheter, the stent delivery catheter comprising the coil stent of claim 1, the stent disposed about the medical balloon;

advancing the catheter in a bodily vessel to a desired location in the body;

causing the stent to expand to a first diameter; and expanding the expandable links to further expand the stent to a second diameter.

28. The method of claim 27 wherein the stent is at least partially self-expanding.

29. The method of claim 27 wherein the stent delivery catheter further comprises a medical balloon and the stent is disposed about the medical balloon.

30. The method of claim 29 wherein the expanding step includes inflating the medical balloon to apply an outward force to the expandable links.

* * * * *